US009682061B2

(12) United States Patent
Lehoux et al.

(10) Patent No.: US 9,682,061 B2
(45) Date of Patent: Jun. 20, 2017

(54) METHODS OF TREATING BACTERIAL INFECTIONS USING ORITAVANCIN

(75) Inventors: Dario Lehoux, Terrebonne (CA); Thomas Parr, Jr., Indianapolis, IN (US); Gregory Moeck, St. Laurent (CA)

(73) Assignee: THE MEDICINES COMPANY, Parsippany, NJ (US)

( * ) Notice: Subject to any disclaimer, the term of this patent is extended or adjusted under 35 U.S.C. 154(b) by 0 days.

(21) Appl. No.: 12/740,571

(22) PCT Filed: Apr. 26, 2010

(86) PCT No.: PCT/US2010/032441
§ 371 (c)(1),
(2), (4) Date: May 4, 2010

(87) PCT Pub. No.: WO2010/129233
PCT Pub. Date: Nov. 11, 2010

(65) Prior Publication Data
US 2012/0035097 A1 Feb. 9, 2012

Related U.S. Application Data

(60) Provisional application No. 61/173,451, filed on Apr. 28, 2009.

(51) Int. Cl.
*A61K 38/12* (2006.01)
*A61K 38/14* (2006.01)
*A61K 31/35* (2006.01)

(52) U.S. Cl.
CPC .............. *A61K 31/35* (2013.01); *A61K 38/12* (2013.01); *A61K 38/14* (2013.01)

(58) Field of Classification Search
CPC ........... A61K 38/12; A61K 38/14; C07K 7/64
See application file for complete search history.

(56) References Cited

U.S. PATENT DOCUMENTS

| 2003/0176327 A1* | 9/2003 | Cassell et al. ................ 514/8 |
| 2010/0041585 A1* | 2/2010 | Moeck .................. A61K 31/00 514/1.1 |
| 2011/0201546 A1 | 8/2011 | Lehoux et al. |

FOREIGN PATENT DOCUMENTS

WO 2009/036121 3/2009

OTHER PUBLICATIONS

Kennedy et al., "Influence of inoculum, medium and serum on the in-vitro susceptibility of coagulase-negative staphylococci to teicoplanin and vancomycin", 1996, Journal of Antimicrobial Chemotherapy, pp. 1103-1109.*

Wasilewski et al. "Equivalence of shorter course therapy with oritavancin vs. vancomycin/cephalexin in complicated skin/skin structure infections (CSSI)" In: Program and abstracts of the 41st interscience conference on antimicrobial agents and chemotherapy Chicago, IL, Dec. 16-19, 2001; p. 1.*
Fetterly et al. "Pharmacokinetics of Oritavancin in Plasma and Skin Blister Fluid following Administration of a 200-Milligram Dose for 3 Days or a Single 800-Milligram Dose", Antimicrobial Agents and Chemotherapy, 2005, pp. 148-152.*
Ziv et al. "Binding of Antibiotics to Bovine and Ovine Serum" Antimicrobial Agents and Chemotherapy, 1972, pp. 206-213.*
Heine et al. ,"Efficacy of Oritavancin in a Murine Model of Bacillys anthracis Spore Inhalation Anthrax", Antimicrobial Agents and Chemotherapy, Sep. 2008, published ahead of print Jul. 7, 2008, pp. 3350-3357.*
Boylan et al., Pharmacodynamics of Oritavancin (LY333328) in Neutropenic-Mouse Thigh Model of *Staphylococcus aureus* Infection, 2003, Antimicrobial Agents and Chemotherapy, pp. 1700-1706.*
Peterson et al.,Influence of Protein Binding of Antibiotics on Serum Pharmacokinetics and Extravascular Penetration: Clinically Useful Concepts,1980, Reviews of Infectious Diseases, pp. 340-348.*
Bhavnani et al., "Pharmacokinetic-Pharmacodynamic Relationships Describing the Efficacy of Oritavancin in Patients with *Staphylococcus aureus* Bacteremia", Antimicrobial Agents and Chemotherapy, 2006, pp. 994-1000.*
Mercier, R.C. et al., Oritavancin: a new avenue for resistant Gram-positive bacteria, Expert Rev. Anti Infect. Ther. vol. 3, No. 3, 2005, pp. 325-332.
Saleh-Mghir, A. et al., Activity and diffusion of LY333328 in experimental endocarditis due to vancomycin-resistant Enterococcus faecalis, Antimicrobial Agents and Chemotherapy, 1999, vol. 43, No. 1, pp. 115-120.
McKay, G. et al., Impact of human serum albumin (HSA) on oritavancin (ORI) in vitro activity against enterococci, Abstracts Book, Interscience Conference on Antimicrobial Agents & Chemotherapy, American Society for Microbiology, 2008, vol. 48, p. 142.
Supplementary European Search Report dated Aug. 30, 2012, from the European Patent Office in corresponding European Application No. 10772493.2.
Poster entitled: "Equivalence of Shorter Course Therapy with Oritavancin Compared to Vancomycin/Cephalexin in Complicated Skin/Skin Structure Infections (CSSI)" by M. Wasilewski et al., presented at 41st Interscience Conference on Antimicrobial Agents and Chemotherapy, Chicago, IL, Dec. 16-19, 2001.
Rowe, P.A., et al. Protein Binding of 14C-Oritavancin. Abstracts of the 41st Interscience Conference on Antimicrobial Agents and Chemotherapy, Chicago, Illinois, USA, Dec. 16-19, 2001. Abstract: A-2193.
Rubino, C.M. et al., Oritavancin Population Pharmacokinetics in Healthy Subjects and Patients with Complicated Skin and Skin Structure Infections or Bacteremia. Antimicrob. Agents Chemother, 53(10):4422-4428 (2009).
Arhin, F.F. et al., Assessment of Oritavancin Serum Protein Binding Across Species. 20th European Congress of Clinical Microbiology and Infectious Diseases, Vienna, Austria, Apr. 10-13, 2010. P-1239.

(Continued)

*Primary Examiner* — Lianko Garyu
(74) *Attorney, Agent, or Firm* — Wenderoth, Lind & Ponack, L.L.P.

(57) ABSTRACT

The present invention is directed to methods of treating a bacterial infection in a subject through the administration of a therapeutically effective amount of a glycopeptide antibiotic to a subject having a bacterial infection. The effective amount of the glycopeptide antibiotic that is administered to the subject provides a fraction of the glycopeptide antibiotic administered to the subject bound to serum proteins within the subject and within a selected range.

17 Claims, No Drawings

(56) References Cited

OTHER PUBLICATIONS

Arhin, F.F. et al., Assessment of Oritavancin Serum Protein Binding Across Species. Antimicrob. Agents Chemother, 54(8):3481-3483 (2010).

McKay, G.A. et al., Impact of Human Serum Albumin on Oritavancin In Vitro Activity against Enterococci. Antimicrob, Agents Chemother. 53(6):2687-2689 (2009).

Arhin, F.F. et al., Impact of human serum albumin on oritavancin in vitro activity against Staphylococcus aureus. Diagn. Microbiol. Infect. Dis. 65(2):207-10 (2009).

Arhin, F.F. et al., Impact of human serum albumin on oritavancin in vitro activity against *Staphylococcus aureus*. 47th Interscience Conference on Antimicrobial Agents and Chemotherapy (ICAAC). Chicago, IL 2007. E1621.

Belanger O et al., Quantitative determination and pharmacokinetics of oritavancin in rabbit serum and tibia. 18th European Congress of Clinical Microbiolgoy and Infectious Diseases. Barcelona, Spain. 2008. P-1061.

McKay, G.A. et al., Evaluation of oritavancin activity in vitro in the presence of human and mouse serum. 19th European Congress of Clinical Microbiology and Infectious Diseases. Helsinki, Finland. 2009. P-1854.

* cited by examiner

US 9,682,061 B2

METHODS OF TREATING BACTERIAL INFECTIONS USING ORITAVANCIN

BACKGROUND OF THE INVENTION

Glycopeptide and lipoglycopeptide antibiotics are a class of biologically produced or semi-synthetic antimicrobial agents which affect bacterial cell wall and/or membrane integrity (Williams et al., Angewandte Chemie International Edition in English 38:1172-1193 (1999); Nicolaou et al., Angewandte Chemie International Edition in English 38:2097-2152 (1999); Kahne et al., Chemical Reviews 105: 425-448 (2005); Pace et al., Biochemical Pharmacology 71:968-980 (2006)). The best known glycopeptide and lipoglycopeptide antibiotics include vancomycin, teicoplanin, oritavancin (U.S. Pat. No. 5,840,684), dalbavancin (U.S. Pat. No. 5,750,509) and telavancin (U.S. Pat. No. 6,635,618). The first two drugs were proven clinically and microbiologically to have potent activity against gram-positive organisms and the latter three drugs are in clinical trials. Oritavancin, dalbavancin and telavancin possess extremely attractive pharmacological profiles with potent activity against gram-positive organisms, including methicillin-resistant Staphylococcus aureus, intermediate and fully vancomycin-resistant Staphylococcus aureus, vancomycin-resistant Enterococcus spp., and Streptococcus spp.

Oritavancin is a semi-synthetic lipoglycopeptide in clinical development against serious gram-positive infections. It exerts activity against methicillin-resistant Staphylococcus aureus (MRSA) and vancomycin-resistant enterococci (VRE). The rapidity of its bactericidal activity against exponentially-growing S. aureus (≥3-log reduction within 15 minutes to 2 hours against MSSA, MRSA, and VRSA) is one feature that distinguishes it from the prototypic glycopeptide vancomycin (McKay et al., Time-kill kinetics of oritavancin and comparator agents against Staphylococcus aureus, Enterococcus faecalis and Enterococcus faecium. J Antimicrob Chemother. 2009 Apr. 15. (Epub ahead of print) PubMed PMID: 19369269).

Recent work demonstrated that oritavancin has multiple mechanisms of action that can contribute to cell death of exponentially-growing S. aureus, including inhibition of cell wall synthesis by both substrate-dependent and -independent mechanisms (Allen et al., FEMS Microbiol Rev 26:511-32 (2003); Arhin et al., Newly defined in vitro quality control ranges for oritavancin broth microdilution testing and impact of variation in testing parameters. Diagn Microbiol Infect Dis. 2008 Sep., 62(1):92-5.; Wang et al., Probing the mechanism of inhibition of bacterial peptidoglycan glycosyltransferases by glycopeptide analogs, 47th Interscience Conference on Antimicrobial Agents and Chemotherapy, Chicago, Ill. (2007)), disruption of membrane potential and increasing membrane permeability (McKay et al., Oritavancin Disrupts Transmembrane Potential and Membrane Integrity Concomitantly with Cell Killing in Staphylococcus aureus and Vancomycin-Resistant Enterococci, 46th Interscience Conference on Antimicrobial Agents and Chemotherapy, San Francisco, Calif. (2006)), and inhibition of RNA synthesis (Arhin et al., Effect of Polysorbate-80 on Oritavancin Binding to Plastic Surfaces-Implications for Susceptibility Testing, 17th European Congress of Clinical Microbiology and Infectious Diseases, Munich, Germany (2007)). The ability of oritavancin but not vancomycin to interact with the cell membrane, leading to loss of membrane integrity and collapse of transmembrane potential, correlates with the rapidity of oritavancin bactericidal activity (McKay et al., Oritavancin Disrupts Transmembrane Potential and Membrane Integrity Concomitantly with Cell Killing in Staphylococcus aureus and Vancomycin-Resistant Enterococci, 46th Interscience Conference on Antimicrobial Agents and Chemotherapy, San Francisco, Calif. (2006)).

BRIEF SUMMARY OF THE INVENTION

Treating

The present invention is generally directed to a method of treating a bacterial infection in a subject, comprising administering a therapeutically effective amount of a glycopeptide antibiotic to a subject having a bacterial infection, wherein the glycopeptide antibiotic is oritavancin, or a pharmaceutically acceptable salt, hydrate, or solvate thereof, or a mixture thereof, and wherein the effective amount of the glycopeptide antibiotic provides a fraction of glycopeptide antibiotic bound to serum proteins in the subject in the range of about 50% to about 95%. In additional aspects, the effective amount of the glycopeptide antibiotic provides a fraction of glycopeptide antibiotic bound to serum proteins in the range of about 80% to about 90%, about 70% to about 90%, or about 55% to about 65%.

In this embodiment, the fraction of glycopeptide antibiotic bound to serum proteins may be determined about 30 minutes after completion of the administration of the glycopeptide antibiotic. In equally preferred aspects, the determination may be performed about 3 hours, about 6 hours, about 9 hours, about 12 hours, about 15 hours, about 18 hours, about 21 hours, or about 24 hours after completion of the administration of the glycopeptide antibiotic.

The present invention is further generally directed to a method of treating a bacterial infection in a subject, comprising administering a therapeutically effective amount of a glycopeptide antibiotic to a subject having a bacterial infection, wherein the glycopeptide antibiotic is oritavancin, or a pharmaceutically acceptable salt, hydrate, or solvate thereof, or a mixture thereof, and wherein the effective amount of the glycopeptide antibiotic provides a mean fraction of glycopeptide antibiotic bound to serum proteins in the subject in the range of about 50% to about 95% from a mean of about 30 minutes to about 24 hours after completion of administration of the glycopeptide antibiotic. In additional aspects, the effective amount of the glycopeptide antibiotic provides a mean fraction of glycopeptide antibiotic bound to serum proteins in the range of about 80% to about 90%, about 70% to about 90%, or about 55% to about 65%.

In this embodiment, the mean fraction of glycopeptide antibiotic bound to serum proteins may be determined by calculating the mean value of nine measurements, the first measurement being the fraction of glycopeptide antibiotic bound to serum proteins at about 30 minutes after completion of the administration of the glycopeptide antibiotic, the second through seventh measurements being determined at about 1.5 hours, at about 2.5 hours, at about 3.5 hours, at about 4.5 hours, at about 5.5 hours and at about 6.5 hours after completion of the administration, respectively, the eighth measurement being determined at about 12 hours after completion of the administration, and the ninth measurement being determined at about 24 hours after completion of the administration.

The present invention is additionally generally directed to a method of treating a bacterial infection in a subject, comprising administering a therapeutically effective amount of a glycopeptide antibiotic to a subject having a bacterial infection, wherein the glycopeptide antibiotic is oritavancin, or a pharmaceutically acceptable salt, hydrate, or solvate thereof, or a mixture thereof, and wherein the effective amount of the glycopeptide antibiotic provides a mean fraction of glycopeptide antibiotic bound to serum proteins in the subject in a range of about 50% to about 95% for at least about 30 minutes after completion of administration.

In additional aspects, the effective amount of the glycopeptide antibiotic provides a mean fraction of glycopeptide antibiotic bound to serum proteins in the range of about 80% to about 90%, about 70% to about 90%, or about 55% to about 65%. In this embodiment, the mean fraction of glycopeptide antibiotic bound to serum proteins may also persist in the noted ranges for at least about 1, 2, 3, 4, 5, 6, 7, 8, 9, 10, 11 or 12, or more, hours after completion of the administration.

Preventing

The present invention is also generally directed to a method of preventing a bacterial infection in a subject, comprising administering to a subject at risk of a bacterial infection an amount of a glycopeptide antibiotic sufficient to prevent the bacterial infection, wherein the glycopeptide antibiotic is oritavancin, or a pharmaceutically acceptable salt, hydrate, or solvate thereof, or a mixture thereof, and wherein the amount sufficient to prevent a bacterial infection provides a fraction of glycopeptide antibiotic bound to serum proteins in the subject in the range of about 50% to about 95%. In additional aspects, the amount of the glycopeptide antibiotic provides a fraction of glycopeptide antibiotic bound to serum proteins in the range of about 80% to about 90%, about 70% to about 90%, or about 55% to about 65%.

In this embodiment, the fraction of glycopeptide antibiotic bound to serum proteins may be determined about 30 minutes after completion of the administration of the glycopeptide antibiotic. In equally preferred aspects, the determination may be performed about 3 hours, about 6 hours, about 9 hours, about 12 hours, about 15 hours, about 18 hours, about 21 hours, or about 24 hours after completion of the administration of the glycopeptide antibiotic.

The present invention is further also generally directed to a method of preventing a bacterial infection in a subject, comprising administering to a subject at risk of a bacterial infection an amount of a glycopeptide antibiotic sufficient to prevent the bacterial infection, wherein the glycopeptide antibiotic is oritavancin, or a pharmaceutically acceptable salt, hydrate, or solvate thereof, or a mixture thereof, and wherein the amount sufficient to prevent a bacterial infection provides a mean fraction of glycopeptide antibiotic bound to serum proteins in the subject in the range of about 50% to about 95% from a mean of about 30 minutes to about 24 hours after completion of administration of the glycopeptide antibiotic. In additional aspects, the amount of the glycopeptide antibiotic provides a mean fraction of glycopeptide antibiotic bound to serum proteins in the range of about 80% to about 90%, about 70% to about 90%, or about 55% to about 65%.

In this embodiment, the mean fraction of glycopeptide antibiotic bound to serum proteins may be determined by calculating the mean value of nine measurements, the first measurement being the fraction of glycopeptide antibiotic bound to serum proteins at about 30 minutes after completion of the administration of the glycopeptide antibiotic, the second through seventh measurements being determined at about 1.5 hours, at about 2.5 hours, at about 3.5 hours, at about 4.5 hours, at about 5.5 hours and at about 6.5 hours after completion of the administration, respectively, the eighth measurement being determined at about 12 hours after completion of the administration, and the ninth measurement being determined at about 24 hours after completion of the administration.

The present invention is additionally generally directed to a method of preventing a bacterial infection in a subject, comprising administering to a subject at risk of a bacterial infection an amount of a glycopeptide antibiotic sufficient to prevent the bacterial infection, wherein the glycopeptide antibiotic is oritavancin, or a pharmaceutically acceptable salt, hydrate, or solvate thereof, or a mixture thereof, and wherein the effective amount of the glycopeptide antibiotic provides a mean fraction of glycopeptide antibiotic bound to serum proteins in the subject in a range of about 50% to about 95% for at least about 30 minutes after completion of administration.

In additional aspects, the effective amount of the glycopeptide antibiotic provides a mean fraction of glycopeptide antibiotic bound to serum proteins in the range of about 80% to about 90%, about 70% to about 90%, or about 55% to about 65%. In this embodiment, the mean fraction of glycopeptide antibiotic bound to serum proteins may also persist in the noted ranges for at least about 1, 2, 3, 4, 5, 6, 7, 8, 9, 10, 11 or 12, or more, hours after completion of the administration.

Prophylaxis

The present invention is additionally generally directed to a method for providing prophylaxis of a bacterial infection in a subject, comprising administering to a subject having a bacterial infection an amount of a glycopeptide antibiotic sufficient to achieve prophylaxis of the bacterial infection, wherein the glycopeptide antibiotic is oritavancin, or a pharmaceutically acceptable salt, hydrate, or solvate thereof, or a mixture thereof, and wherein the amount sufficient to achieve prophylaxis provides a fraction of glycopeptide antibiotic bound to serum proteins in the subject in the range of about 50% to about 95%. In additional aspects, the amount of the glycopeptide antibiotic provides a fraction of glycopeptide antibiotic bound to serum proteins in the range of about 80% to about 90%, about 70% to about 90%, or about 55% to about 65%.

In this embodiment, the fraction of glycopeptide antibiotic bound to serum proteins may be determined about 30 minutes after completion of the administration of the glycopeptide antibiotic. In equally preferred aspects, the determination may be performed about 3 hours, about 6 hours, about 9 hours, about 12 hours, about 15 hours, about 18 hours, about 21 hours, or about 24 hours after completion of the administration of the glycopeptide antibiotic.

The present invention is further generally directed to a method for providing prophylaxis of a bacterial infection in a subject, comprising administering to a subject having a bacterial infection an amount of a glycopeptide antibiotic sufficient to achieve prophylaxis of the bacterial infection, wherein the glycopeptide antibiotic is oritavancin, or a pharmaceutically acceptable salt, hydrate, or solvate thereof, or a mixture thereof, and wherein the amount sufficient to achieve prophylaxis provides a mean fraction of glycopeptide antibiotic bound to serum proteins in the subject in the range of about 50% to about 95% from a mean of about 30 minutes to about 24 hours after completion of administration of the glycopeptide antibiotic. In additional aspects, the amount of the glycopeptide antibiotic provides a mean fraction of glycopeptide antibiotic bound to serum proteins in the range of about 80% to about 90%, about 70% to about 90%, or about 55% to about 65%.

In this embodiment, the mean fraction of glycopeptide antibiotic bound to serum proteins may be determined by calculating the mean value of nine measurements, the first measurement being the fraction of glycopeptide antibiotic bound to serum proteins at about 30 minutes after completion of the administration of the glycopeptide antibiotic, the second through seventh measurements being determined at about 1.5 hours, at about 2.5 hours, at about 3.5 hours, at about 4.5 hours, at about 5.5 hours and at about 6.5 hours after completion of the administration, respectively, the eighth measurement being determined at about 12 hours after completion of the administration, and the ninth measurement being determined at about 24 hours after completion of the administration.

The present invention is additionally generally directed to a method for providing prophylaxis of a bacterial infection in a subject, comprising administering to a subject having a bacterial infection an amount of a glycopeptide antibiotic sufficient to achieve prophylaxis of the bacterial infection, wherein the glycopeptide antibiotic is oritavancin, or a pharmaceutically acceptable salt, hydrate, or solvate thereof, or a mixture thereof, and wherein the effective amount of the glycopeptide antibiotic provides a mean fraction of glycopeptide antibiotic bound to serum proteins in the subject in a range of about 50% to about 95% for at least about 30 minutes after completion of administration.

In additional aspects, the effective amount of the glycopeptide antibiotic provides a mean fraction of glycopeptide antibiotic bound to serum proteins in the range of about 80% to about 90%, about 70% to about 90%, or about 55% to about 65%. In this embodiment, the mean fraction of glycopeptide antibiotic bound to serum proteins may also persist in the noted ranges for at least about 1, 2, 3, 4, 5, 6, 7, 8, 9, 10, 11 or 12, or more, hours after completion of the administration.

The present invention is also generally directed to a method of administering a glycopeptide antibiotic to a subject, comprising administering a glycopeptide antibiotic to a subject in need thereof to achieve a pharmacokinetic profile for the glycopeptide antibiotic comprising a mean steady state serum protein binding of at least about 50% for the glycopeptide antibiotic after administration, wherein the glycopeptide antibiotic is oritavancin, or a pharmaceutically acceptable salt, hydrate, or solvate thereof, or a mixture thereof.

In particular aspects, the subject has a bacterial infection or the subject is at risk of developing a bacterial infection. The mean steady state serum protein binding by the glycopeptide antibiotic may also be at least about 55%, 60%, 65%, 70%, 75%, 80%, 85%, 90% or 95%. In this embodiment, the mean steady state serum protein binding by the glycopeptide antibiotic may persist for at least about 1, 2, 3, 4, 5, 6, 7, 8, 9, 10, 11 or 12, or more, hours after completion of the administration.

In each aspect and embodiment of the present invention, the fraction of glycopeptide antibiotic bound to serum proteins may be determined using any appropriate method of measuring the amount of a glycopeptide antibiotic bound to serum proteins. Such methods may include, for example, direct measurements by equilibrium dialysis, ultra-centrifugation or ultra-filtration, and indirect measurements by in vitro assaying of serum-induced changes in drug minimal inhibitory concentrations (MICs) and area under bacterial kill curves (AUCs).

In each aspect and embodiment of the present invention, the glycopeptide antibiotic is preferably administered in the form of a pharmaceutical composition comprising the glycopeptide antibiotic and a pharmaceutically acceptable carrier or diluent.

As indicated herein, in each aspect and embodiment of the present invention, the glycopeptide antibiotic is oritavancin, or a pharmaceutically acceptable salt, hydrate, or solvate thereof, or a mixture thereof.

In each aspect and embodiment of the present invention, the bacterial infection may be a Complicated Skin and Skin Structure Infection (cSSSI), or one or more of the specific bacterial infections described herein.

In each aspect and embodiment of the present invention, administration of the glycopeptide antibiotic may be via intravenous administration or oral administration, or one of the other suitable means of administration described herein.

DETAILED DESCRIPTION OF THE INVENTION

The present invention is generally directed to a method of treating a bacterial infection in a subject, comprising administering a therapeutically effective amount of a glycopeptide antibiotic to a subject having a bacterial infection, wherein the glycopeptide antibiotic is oritavancin, or a pharmaceutically acceptable salt, hydrate, or solvate thereof, or a mixture thereof, and wherein the effective amount of the glycopeptide antibiotic provides a fraction of glycopeptide antibiotic bound to serum proteins in the subject within a selected range.

The present invention is also generally directed to a method of preventing a bacterial infection in a subject, comprising administering to a subject at risk of a bacterial infection an amount of a glycopeptide antibiotic sufficient to prevent the bacterial infection, wherein the glycopeptide antibiotic is oritavancin, or a pharmaceutically acceptable salt, hydrate, or solvate thereof, or a mixture thereof, and wherein the amount sufficient to prevent a bacterial infection provides a fraction of glycopeptide antibiotic bound to serum proteins in the subject within a selected range.

The present invention is further generally directed to a method for providing prophylaxis of a bacterial infection in a subject, comprising administering to a subject having a bacterial infection an amount of a glycopeptide antibiotic sufficient to achieve prophylaxis of the bacterial infection, wherein the glycopeptide antibiotic is oritavancin, or a pharmaceutically acceptable salt, hydrate, or solvate thereof, or a mixture thereof, and wherein the amount sufficient to achieve prophylaxis provides a fraction of glycopeptide antibiotic bound to serum proteins in the subject within a selected range.

In each of these aspects of the invention, the selected range of glycopeptide antibiotic bound to serum proteins in the subject can be varied depending, for example, on the nature of the infection being treated, but in different aspects the range may be, for example, about 50% to about 60%, about 55% to about 65%, about 60% to about 70%, about 65% to about 75%, about 70% to about 80%, about 75% to about 85%, about 80% to about 90%, or about 85% to about 95% of the total amount of glycopeptide antibiotic administered to the subject. Broader ranges are also contemplated and include ranges of about 50% to about 70%, about 60% to about 80%, about 70% to about 90%, about 60% to about 90%, and about 50% to about 95%.

In each of these aspects of the invention, the fraction of glycopeptide antibiotic determined as being bound to serum proteins will vary from patient to patient, and will also vary depending on the time point at which the fraction bound is determined. Therefore, in addition to assaying at one particular time point in a subject, a range of values may be determined for a particular subject and the methods of the present invention may be based on ranges of value.

The time point at which the fraction of glycopeptide antibiotic bound to serum proteins is determined is not particularly critical. However, the time at which the determination is performed can be correlated with certain pharmacokinetic time points known for a particular glycopeptide antibiotic, such as the time of a peak concentration in serum. Suitable time points at which the determination is made in the present invention include about 30 minutes after completion of the administration of the glycopeptide antibiotic, as well as each time points increasing by about 30 minutes there from, such as about 1 hour, about 1.5 hours, about 2 hours, about 2.5 hours, etc., up to about 24 hours after completion of the administration.

The present invention is further generally directed to a method of treating a bacterial infection in a subject, comprising administering a therapeutically effective amount of a glycopeptide antibiotic to a subject having a bacterial infection, wherein the glycopeptide antibiotic is oritavancin, or a pharmaceutically acceptable salt, hydrate, or solvate thereof, or a mixture thereof, and wherein the effective amount of the glycopeptide antibiotic provides a mean fraction of glycopeptide antibiotic bound to serum proteins in the subject within a selected range over a selected period of time.

The present invention is also generally directed to a method of preventing a bacterial infection in a subject, comprising administering to a subject at risk of a bacterial infection an amount of a glycopeptide antibiotic sufficient to prevent the bacterial infection, wherein the glycopeptide antibiotic is oritavancin, or a pharmaceutically acceptable salt, hydrate, or solvate thereof, or a mixture thereof, and wherein the amount sufficient to prevent a bacterial infection provides a mean fraction of glycopeptide antibiotic bound to serum proteins in the subject within a selected range over a selected period of time.

The present invention is additionally generally directed to a method for providing prophylaxis of a bacterial infection in a subject, comprising administering to a subject having a bacterial infection an amount of a glycopeptide antibiotic sufficient to achieve prophylaxis of the bacterial infection, wherein the glycopeptide antibiotic is oritavancin, or a pharmaceutically acceptable salt, hydrate, or solvate thereof, or a mixture thereof, and wherein the amount sufficient to achieve prophylaxis provides a mean fraction of glycopeptide antibiotic bound to serum proteins in the subject within a selected range over a selected period of time.

As above, in each of these aspects of the invention, the selected range of glycopeptide antibiotic bound to serum proteins in the subject can be varied depending, for example, on the nature of the infection being treated, but in different aspects the range may be, for example, about 50% to about 60%, about 55% to about 65%, about 60% to about 70%, about 65% to about 75%, about 70% to about 80%, about 75% to about 85%, about 80% to about 90%, or about 85% to about 95% of the total amount of glycopeptide antibiotic administered to the subject. Broader ranges are also contemplated and include ranges of about 50% to about 70%, about 60% to about 80%, about 70% to about 90%, about 60% to about 90%, and about 50% to about 95%.

In each of these embodiments, the fraction of glycopeptide antibiotic determined as being bound to serum proteins will also vary from patient to patient, and will also vary depending on the time point at which the fraction bound is determined. Therefore, in addition to assaying at one particular time point in a subject, a range of values may be determined for a particular subject and the methods of the present invention may be based on ranges of value As an additional means of monitoring the fraction of glycopeptide antibiotic bound to serum proteins, the fraction bound can be determined as a mean value over a selected period of time. The period of time is not critical, and may, for example, be correlated with certain pharmacokinetic time periods known for a particular glycopeptide antibiotic, such as the time period of a trough after a peak in serum concentration. A suitable selected period of time over which the determination can be made in the present invention includes twice hourly measurements beginning about 30 minutes after completion of the administration of the glycopeptide antibiotic and ending about 24 hours after completion of the administration. "Twice hourly" should be understood to be two separate measurements within an hour, separated by about 30 minutes. Additional suitable selected periods of time include hourly measurements beginning about 30 minutes after completion of the administration of the glycopeptide antibiotic and ending about 24 hours after completion of the administration, and measurements every two hours that begin about 30 minutes after completion of the administration of the glycopeptide antibiotic and end about 24 hours after completion of the administration. In one particular aspect, a selected period of time is twice hourly measurements beginning about 30 minutes after completion of the administration of the glycopeptide antibiotic through about 6.5 hours after completion of the administration, and then measurements at 12 and 24 hours after completion of the administration. Within each selected period of time, a mean value can be calculated from the measurements.

In each aspect and embodiment of the present invention the fraction of glycopeptide antibiotic bound to serum proteins may be determined using any appropriate method of measuring the fraction of a glycopeptide antibiotic bound to serum proteins, including, for example, equilibrium dialysis, ultra-centrifugation or ultra-filtration. Additional means of measuring serum binding include:

measurement of retention time and peak shape in HPLC using serum albumin columns use of dextran-coated charcoal to separate free from albumin-bound antibiotic biological equilibrium dialysis which analyzes partitioning of free analyte into biological membranes/cells such as erythrocytes surface plasmon resonance to measure changes in SPR upon binding of analytes to immobilized albumin or versions thereof nuclear magnetic resonance approaches growth-based approaches such as determination of shifts in minimum inhibitory concentration (MIC) against an indicator strain of bacteria in the presence vs. absence of serum or serum components measurement of killing kinetics (rate, area under the inhibition curve, extent of kill at a fixed time) against an indicator strain of bacteria in the presence vs. absence of serum or serum components.

In equilibrium dialysis, two compartments are separated by a dialysis membrane and both compartments are filled with solution, one with ligand of interest (e.g. antibiotic) and the other with a receptor (albumin and/or other proteins or binding components of interest). The molecular weight cut off (MWCO) of the dialysis membrane is chosen such that it will allow free passage of the desired ligand and prevent passage of the receptor. As the ligand diffuses across the membrane some of it will bind to the receptor and some will remain free in solution. The higher the affinity of the interaction between the receptor and the ligand, the higher the concentration of ligand that will be bound to the receptor at any time. Diffusion of the ligand across the membrane and binding of the ligand continues until equilibrium has been reached. At equilibrium, the concentration of ligand free in solution is the same in both chambers. In the receptor chamber, however, the overall (total) concentration of the ligand is higher due to the bound-ligand component. The concentration of free ligand in the ligand chamber can then be used to determine the binding characteristics of the samples.

In a typical equilibrium dialysis assay using the Rapid Equilibrium Dialysis apparatus (Thermo Scientific), a known concentration (normally bracketing a physiologically-relevant range; e.g. 0.01 to 100 µg/mL) and volume (100-500 µL) of antibiotic in human serum is placed into the sample chamber of the dialysis apparatus. The MWCO of the dialysis membrane in the device, 8,000, excludes albumin and large serum proteins. A known volume (300-750 µL) of buffer such as phosphate-buffered saline is then placed in the buffer compartment. The unit is covered with sealing tape and incubated at 37° C. at approximately 100 rpm on an orbital shaker or 20 rpm on an up-and-down shaker for 4 hours so as to achieve equilibrium. The seal is removed and equal volumes (e.g. 100 µL, 100 µL) are removed from both the buffer and the plasma chambers, transferred to eppendorf tubes and subjected to liquid chromatography/mass spectrometry (LC/MS) analysis for the antibiotic as follows: samples are centrifuged for 10 minutes at 13,000-15,000×g and 50 µL of each is transferred into separate microcentrifuge tubes. A total of 50 µL of plasma is added to the buffer sample, and 50 µL of PBS is added to the collected plasma sample. 300 µL of precipitation buffer (such as cold 90/10 acetonitrile/water with 0.1% formic acid) is added to precipitate protein and release compound. Samples are vortexed vigorously and incubated 30 minutes on ice. Supernatants are transferred to a vial or plate for analysis; appropriate internal standards are added and the antibiotic is quantitated by LC/MS. Alternatively, the supernatant can be dried and the antibiotic reconstituted before LC/MS. The concentration of test compound in the buffer and plasma chambers from peak areas relative to the internal standard are calculated. To calculate the percentage of the test compound bound to serum protein, the following formulae are used: % Free=(Concentration buffer chamber/Concentration plasma chamber)×100% and % Bound=100%−% Free.

A second method for determination of plasma protein binding is ultrafiltration. The principle of the assay is that during centrifugation (or application of pressure), only the low molecular weight analyte in a mixture of analyte plus albumin (or analyte in serum) can pass through an ultrafiltration membrane if the MWCO of the membrane has been chosen to reside between the molecular weights of the analyte and albumin. As in the equilibrium dialysis assay described above, a known concentration and volume of analyte is spiked into a known volume of serum (or a known concentration and volume of purified serum albumin) and the sample is transferred into the ultrafiltration apparatus. A convenient assay platform is the 96-well Millipore Multi-Screen Ultracel-PPB (plasma protein binding) plate with a dialysis membrane having an MWCO of 10,000 and requiring sample volumes in the 100-300 µL range. After ultrafiltration, the analyte in the ultrafiltrate is quantitated by LC/MS as above.

In an ultracentrifugation assay, a mixture of analyte plus albumin (or analyte in serum) is subjected to ultracentrifugation in a manner that sediments protein-bound analyte and leaves free analyte in solution. After the centrifugation step has been completed, supernatant is carefully removed from the ultracentrifugation tubes and analyte is quantitated by LC/MS as above.

In each aspect and embodiment of the present invention, the glycopeptide antibiotic is oritavancin, or a pharmaceutically acceptable salt, hydrate, or solvate thereof, or a mixture thereof. Oritavancin (also termed N-(4-(4-chlorophenyl)benzyl)A82846B and LY333328) has the following Formula I:

Formula I

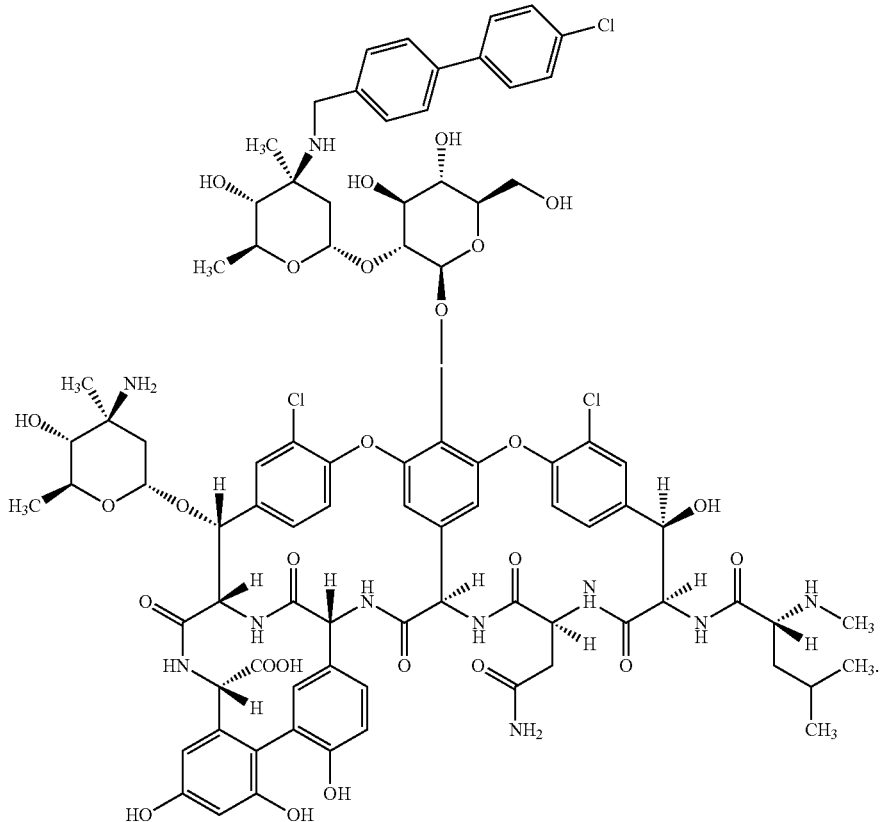

The glycopeptide antibiotics of the present invention are further described in U.S. Pat. No. 5,840,684, incorporated herein by reference in its entirety.

Oritavancin may be used per se or in the form of a pharmaceutically acceptable salt, hydrate, solvate of oritavancin, or as a mixture of one or more thereof. The term "pharmaceutically acceptable salt" refers to non-toxic acid addition salts derived from inorganic and organic acids.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counter-ion forming a part of any salt of this invention is not of a critical nature, so long as the salt as a whole is pharmacologically acceptable and as long as the counter-ion does not contribute undesired qualities to the salt as a whole.

Means for the preparation of oritavancin and analogs thereof may be found, for example, in U.S. Pat. No. 5,840,684, incorporated herein by reference in its entirety.

The glycopeptide antibiotics of the present invention may be also be used in the form of prodrugs, such as glycopeptide antibiotics possessing at least one poly(ethylene glycol) moiety as disclosed in international patent application publication WO 08/118,784 (PCT/US2008/057841), incorporated herein by reference in its entirety. The presence of a poly(ethylene glycol) group attached to a glycopeptide correlates with a higher solubility of the glycopeptide antibiotics in aqueous media. Achieving higher concentrations of glycopeptide antibiotics in aqueous media improves the formulation and reduces the volume of injection, infusion or administration. In addition, the presence of the poly(ethylene) glycol permits the antibiotic to be masked during injection, infusion or administration. The combination of these two factors and the relative lack of toxicity associated with poly(ethylene glycol) allows the side effects observed during the administration of glycopeptide antibiotics to be decreased. In a preferred embodiment, the poly(ethylene glycol) of such prodrugs has an average molecular weight 900 $g.mol^{-1}$ or greater As used herein, a "subject" refers to an animal, such as a mammalian or an avian species, including a human, an ape, a horse, a cow, a sheep, a goat, a dog, and a cat. The subject may have a bacterial infection, may have been exposed to infectious bacteria, may be at risk for developing a bacterial infection, or may be at greater risk than the general population for developing a bacterial infection. Examples of subjects at greater risk for developing a bacterial infection include patients undergoing treatment for bacterial infections whereby normal gut flora is inhibited by antimicrobial therapy, patients with impaired immune function (e.g., immunoglobulin deficiency, splenic dysfunction, splenectomy, HIV infection, impaired leukocyte function, hemoglobinopathies), the elderly, people with certain malignancies (e.g., multiple myeloma, chronic lympocytic leukemia, lymphoma), people at increased occupational risk (e.g., public services workers, such a fire, water, sanitary, police, medical, and laboratory workers, hospital workers), people in closed populations (e.g., prisons, military, nursing homes) and others that have immunological deficiencies that might enhance their susceptibility to bacterial infection.

The methods of the present invention include those performed in vivo, in vitro or ex vivo. The in vitro methods are exemplified, but not limited to, methods performed in a laboratory setting, such as in a cell culture, as well as methods performed on inert objects such as laboratory or hospital equipment and devices, surfaces such as countertops and bench tops. The ex vivo methods are exemplified, but not limited to, methods performed on the surface of the human body, such as on the hands.

In each aspect and embodiment of the present invention, the glycopeptide antibiotic is preferably administered in the form of a pharmaceutical composition comprising the glycopeptide antibiotic and a pharmaceutically acceptable carrier or diluent.

The pharmaceutical compositions of the present invention comprise one or more glycopeptide antibiotics, and one or more of a carrier, diluent and excipient. Suitable carriers, diluents and excipients are well known to those skilled in the art and include saline, buffered saline, dextrose (e.g., 5% dextrose in water), water, glycerol, ethanol, propylene glycol, polysorbate 80 (Tween-80™), 0.002% polysorbate 80 (Tween-80™), poly(ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin; see, e.g., U.S. patent application publication 20060194717), hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium.

Excipients included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavouring agents, coloring agents, administration aids, and combinations thereof.

The compositions may contain common carriers and excipients, such as cornstarch or gelatin, lactose, sucrose, microcrystalline cellulose, kaolin, mannitol, dicalcium phosphate, sodium chloride, alginic acid, croscarmellose sodium, and sodium starch glycolate.

The particular carrier, diluent or excipient used will depend upon the means and purpose for which the active ingredient is being applied.

Pharmaceutically acceptable excipients also include tonicity agents that make the composition compatible with blood. Tonicity agents are particularly desirable in injectable formulations.

The pharmaceutical compositions and glycopeptide antibiotics of the present invention may be formulated, for example, for oral, sublingual, intranasal, intraocular, rectal, transdermal, mucosal, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration. In noted aspects and embodiments of the present invention, administration of the glycopeptide antibiotic is via intravenous administration or oral administration.

Formulations for parenteral administration can be in the form of aqueous or non-aqueous isotonic sterile injection solutions, suspensions or fat emulsions. The parenteral form used for injection must be fluid to the extent that easy syringability exists. These solutions or suspensions can be prepared from sterile concentrated liquids, powders or granules.

Excipients used in parenteral preparations also include, without limitation, stabilizing agents (e.g. carbohydrates, amino acids and polysorbates, such as 5% dextrose), solubilizing agents (e.g. cetrimide, sodium docusate, glyceryl monooleate, polyvinylpyrolidone (PVP) and polyethylene glycol (PEG)), surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vasoconstrictors for prolongation and agents that increase tissue permeability), and combinations thereof.

Parenteral formulations using hydrophobic carriers include, for example, fat emulsions and formulations containing lipids, lipospheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In another embodiment, the parenteral unit dosage form of glycopeptide antibiotics can be a ready-to-use solution of the glycopeptide antibiotic in a suitable carrier in sterile, hermetically sealed ampoules or in sterile pre-loaded syringes. The suitable carrier optionally comprises any of the above-mentioned excipients.

Alternatively, the unit dosage of the glycopeptide antibiotics of the present invention can be in a concentrated liquid, powder or granular form for ex tempore reconstitution in the appropriate pharmaceutically acceptable carrier, such as sterile water, at the time of delivery. In addition to the above-mentioned excipients, powder forms optionally include bulking agents (e.g. mannitol, glycine, lactose, sucrose, trehalose, dextran, hydroxyethyl starch, ficoll and gelatin), and cryo or lyoprotectants.

In intravenous (IV) use, a sterile formulation of the pharmaceutical compositions of the present invention and optionally one or more additives, including solubilizers or surfactants, can be dissolved or suspended in any of the commonly used intravenous fluids and administered by infusion. Intravenous fluids include, without limitation, physiological saline, phosphate buffered saline, 5% dextrose in water, 0.002% polysorbate 80 (Tween-80™) in water or Ringer'™ solution.

In intramuscular preparations, a sterile formulation of the pharmaceutical compositions of the present invention can be dissolved and administered in a pharmaceutical diluent such as Water-for-Injection (WFI), physiological saline or 5% dextrose in water. A suitable insoluble form of the pharmaceutical compositions may be prepared and administered as a suspension in an aqueous base or a pharmaceutically acceptable oil base, e.g. an ester of a long chain fatty acid such as ethyl oleate.

For oral use, the oral pharmaceutical composition may be made in the form of a unit dosage containing a therapeutically-effective amount of the pharmaceutical compositions. Solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, tablets, capsules, suspensions or liquid syrups or elixirs, wafers and the like. For general oral administration, excipient or additives include, but are not limited to inert diluents, fillers, disintegrating agents, binding agents, wetting agents, lubricating agents, sweetening agents, flavoring agents, coloring agents and preservatives.

For therapeutic purposes, the tablets and capsules can contain, in addition to the glycopeptide antibiotics, conventional carriers such as: inert diluents (e.g., sodium and calcium carbonate, sodium and calcium phosphate, and lactose), binding agents (e.g., acacia gum, starch, gelatin, sucrose, polyvinylpyrrolidone (Povidone), sorbitol, tragacanth methylcellulose, sodium carboxymethylcellulose, hydroxypropyl methylcellulose, and ethylcellulose), fillers (e.g., calcium phosphate, glycine, lactose, maize-starch, sorbitol, or sucrose), wetting agents, lubricating agents (e.g., metallic stearates, stearic acid, polyethylene glycol, waxes, oils, silica and colloical silica, silicon fluid or talc), disintegrating agents (e.g., potato starch, corn starch and alginic acid), flavouring (e.g. peppermint, oil of wintergreen, fruit flavoring, cherry, grape, bubblegum, and the like), and coloring agents. Carriers may also include coating excipients such as glyceryl monostearate or glyceryl distearate, to delay absorption in the gastrointestinal tract.

In a particular oral formulation, the glycopeptide antibiotics of the present invention may be in the form of a capsule containing the glycopeptide antibiotic, gelatin, iron oxide, polyethylene glycol, titanium dioxide, and one or more other inactive ingredients. Suitable amounts of the glycopeptide antibiotic in the capsule may range from about 10 to about 3000 mg, with preferred amounts including about 100, 125, 150, 175, 200, 225, 250, 275, 300, 350, 400, 450, 500, 550, 600, 650, 700, 750, 800, 850, 900, 950, 1000, 1050, 1100, 1150, 1200, 1250, 1300, 1350, 1400, 1450 and 1500 mg of the glycopeptide antibiotic. The oral formulations may also include polyethylene glycol (PEG), wherein the PEG is about PEG200 to about PEG8000, preferably about PEG400 to about PEG6000.

Oral liquid preparations, generally in the form of aqueous or oily solutions, suspensions, emulsions or elixirs, may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, microcrystalline cellulose, methyl or propyl para-hydroxybenzoate, propylene glycol, sorbitol, or sorbic acid.

For topical use, the pharmaceutical compositions of present invention can also be prepared in suitable forms to be applied to the skin, or mucus membranes of the nose and throat, and can take the form of creams, ointments, nasal drops, liquid sprays or inhalants, lozenges, or throat paints. Such topical formulations further can include chemical compounds such as dimethylsulfoxide (DMSO) to facilitate surface penetration of the active ingredient. For application to the eyes or ears, the pharmaceutical compositions can be presented in liquid or semi-liquid form formulated in hydrophobic or hydrophilic bases as ointments, creams, lotions, paints or powders. For rectal administration the pharmaceutical compositions can be administered in the form of suppositories admixed with conventional carriers such as cocoa butter, wax or other glyceride.

In a preferred intravenous (IV) formulation for use in the methods of the present invention, the glycopeptide antibiotic is administered in a dosage of between about 10 mg and 2000 mg, preferably about 10, 20, 30, 40, 50, 60, 70, 80, 90, 100, 125, 150, 175, 200, 225, 250, 275, 300, 325, 350, 375, 400, 450, 500, 600, 700, 800, 900, 1000, 1100, 1200, 1300, 1400, 1500 or more mg, by IV infusion over approximately 60, 90, 120, 150, 180, 210 or more minutes, every 6, 12, 18 or 24 hours for 1, 2, 3, 4, 5, 6, 7, 8, 9, 10 or more days. In these embodiments, the glycopeptide antibiotic may be reconstituted in sterile water for injection (WFI). Further in this embodiment, the glycopeptide antibiotic may be diluted in 5% dextrose in water (D5W) to a total volume of at least 250 mL. Preferably the resultant concentration is no more than 0.8 mg/mL for a 200-mg dose, 1.0 mg/mL for a 250-mg dose, and 1.2 mg/mL for a 300-mg dose.

In a preferred oral formulation for use in the methods of the present invention, the glycopeptide antibiotic is administered in an oral dosage of between about 0.5 to about 100 mg per kg body weight of the subject to which the oral formulation is being administered, more preferably about 5 to about 30 mg per kg body weight, including about 5, 10, 15, 20, 25 and 30 mg per kg body weight. The course of treatment via oral administration may be a single dose or multiple doses. When multiple doses are administered orally, administration may be once, twice, thrice or more times per day. A course of oral treatment may be for one or more days, such as two, three, four, five, six, seven, eight, nine, ten or more days. In one embodiment, the glycopeptide antibiotic may be formulated in 10% hydroxypropyl beta-cyclodextrin. In a further embodiment the glycopeptide antibiotic may be formulated in 85% polyethylene glycol 400 (PEG400) in sterile water. The oral formulation may be in the form of a liquid to be drunk by the subject, in the form of a capsule containing the glycopeptide antibiotic formulation, or other means known to the skilled artisan for administering an oral formulation.

In each of the methods of the present invention, the glycopeptide antibiotic may be used alone, in combination with one or more additional glycopeptides, such as vancomycin, in combination with one or more other antibiotic agents or as a combination of two or more glycopeptides and one or more other antibiotic agents. In particular, in each of the methods of the present invention the glycopeptide antibiotic may be (a) used alone, (b) used in combination with one or more additional glycopeptides, such as vancomycin, (c) used in combination with one or more other antibiotic agents, or (d) used as a combination of (i) the glycopeptide antibiotic, (ii) one or more other glycopeptides, and (iii) one or more other antibiotic agents.

The other antibiotic agents include fluoroquinolones (including ciprofloxacin), tetracyclines (including doxycycline), macrolides (including erythromycin, cethromycin, azithromycin and clarithromycin), β-lactams (including penicillin, imipenem and ampicillin), ansamycins (including rifampin), phenicols (including chloramphenicol), streptogramins (including quinupristin-dalfopristin), aminoglycosides (including gentamicin), oxazolidinones (including linezolid), tetracyclines, glycylglycines (including tigecycline), cyclic lipopeptides (including daptomycin) and lincosamines (including clindamycin).

Specific examples of other antibiotic agents include fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, a minocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent. The skilled artisan will understand that concurrent administration includes administration of the glycopeptide antibiotic and second antibacterial agent at the same time or serially but during the same course of administration.

The terms "dose", "unit dose", "unit dosage", or "effective dose" refer to physically discrete units that contain a predetermined quantity of active ingredient calculated to produce a desired therapeutic effect. These terms are synonymous with the therapeutically effective amounts and amounts sufficient to achieve the stated goals of the methods disclosed herein.

The therapeutically effective amount of the glycopeptide antibiotics of the present invention and the amounts sufficient to achieve the stated goals of the methods disclosed herein vary depending upon the physical characteristics of the subject, the severity of the subject's symptoms, the identity of the infection being treated or prevented, the formulation and the means used to administer the drug, and the method being practiced. The specific dose for a given subject is usually set by the judgment of the attending physician. However, a therapeutically effective and/or sufficient amount of the glycopeptide antibiotics of the present invention, including oritavancin, is typically between about 0.5 mg/kg body weight to 100 mg/kg body weight, preferably from 1 to 50 mg/kg, more preferably from 5 to 30 mg/kg, regardless of the formulation. In equally preferred embodiments, a therapeutically effective amount used for a single dose is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 mg/kg body weight, regardless of the formulation. In some situations, a dose less than 0.5 mg/kg body weight or greater than 100 mg/kg body weight may be effective.

Suitable frequencies of administration may vary based on whether administration is for the purposes of treatment, prophylaxis or prevention. Administration frequencies of doses for the treatment of a subject having a bacterial infection, prophylaxis or prevention of bacterial infection include 4, 3, 2 or once daily, every other day, every third day, every fourth day, every fifth day, every sixth day, once weekly, every eight days, every nine days, every ten days, bi-weekly, monthly and bi-monthly. In certain methods and embodiments of the present invention a single dose or infrequent dose (e.g., 2, 3, 4, 5 or six doses) can be sufficient to achieve the stated goals of the methods claimed herein. In other embodiments, the course of treatment may required the administration of many doses over many days, such as administration of a dose 4, 3, 2 or once daily over 1, 2, 3, 4, 5, 6, 7, 8, 9, 10, 11, 12, 13, 14, 15 or more days.

Depending on the means of administration, the dosage may be administered all at once, such as with an oral formulation in a capsule, or slowly over a period of time, such as with an intravenous administration. For slower means of administration, the administering period can be a matter of minutes, such as about 5, 10, 15, 20, 25, 30, 35, 40, 45, 50, 55, 60, 65, 70, 75, 80, 85, 90, 95, 100, 105, 110, 115, 120, 135, 150, 165, 180, 195, 210 or more minutes, or a period of hours, such as about 0.5, 1, 1.5, 2, 2.5, 3, 3.5, 4, 4.5, 5 or more hours.

As used herein, the terms "inhibit", "inhibiting" and "inhibition" have their ordinary and customary meanings, and include one or more of inhibiting growth or a function of bacteria, inhibiting growth of a vegetative form of bacteria, inhibiting a function of a vegetative form of bacteria, inhibiting propagation of bacteria, inhibiting bacterial sporulation, inhibiting activation of a bacterial spore, inhibiting germination of a bacterial spore, and inhibiting outgrowth of a bacterial spore. Such inhibition is an inhibition of about 1% to about 100% of the particular activity versus the activity in a subject to which a pharmaceutical composition or glycopeptide antibiotic of the present invention has not been administered. Preferably, the inhibition is an inhibition of 100%, 99%, 98%, 97%, 96%, 95%, 90%, 80%, 70%, 60%, 50%, 40%, 30%, 20%, 10%, 5% or 1% of the activity versus a subject to which a pharmaceutical composition or glycopeptide antibiotic of the present invention has not been administered. As used herein, "spore" refers to both the conventionally used terms "spore" and "endospore."

As used herein, the terms "treating" and "treatment" have their ordinary and customary meanings, and include one or more of, ameliorating a symptom of a bacterial infection in a subject, blocking or ameliorating a recurrence of a symptom of a bacterial infection in a subject, decreasing in severity and/or frequency a symptom of a bacterial infection in a subject, stasis, decreasing, or inhibiting growth of a vegetative form of bacteria in a subject, inhibiting bacterial sporulation in a subject, inhibiting activation of a bacterial spore in a subject, inhibiting germination of a bacterial spore in a subject, and inhibiting outgrowth of a bacterial spore in a subject. Treatment means ameliorating, blocking, reducing, decreasing or inhibiting by about 1% to about 100% versus a subject to which a pharmaceutical composition or glycopeptide antibiotic of the present invention has not been administered. Preferably, the ameliorating, blocking, reducing, decreasing or inhibiting is 100%, 99%, 98%, 97%, 96%, 95%, 90%, 80%, 70%, 60%, 50%, 40%, 30%, 20%, 10%, 5% or 1% versus a subject to which a pharmaceutical composition or glycopeptide antibiotic of the present invention has not been administered.

As used herein, the terms "preventing" and "prevention" have their ordinary and customary meanings, and includes one or more of preventing colonization of bacteria in a subject, preventing an increase in the growth of a population of bacteria in a subject, preventing activation, germination or outgrowth of bacterial spores in a subject, preventing sporulation of bacteria in a subject, preventing development of a disease caused by bacteria in a subject, and preventing symptoms of a disease caused by bacteria in a subject. As used herein, the prevention lasts at least about 0.5, 1, 2, 3, 4, 5, 6, 7, 10, 12, 15, 20, 25, 30, 35, 40 or more days after administration of a pharmaceutical composition or glycopeptide antibiotic of the present invention.

As used herein, "prophylaxis" includes inhibiting the development of a productive or progressive infection by bacteria in a subject, where the prophylaxis lasts at least about 0.5, 1, 2, 3, 4, 5, 6, 7, 10, 12, 15, 20, 25, 30, 35, 40 or more days after administration of a pharmaceutical composition or glycopeptide antibiotic of the present invention Inhibition against development of a productive or progressive infection by a bacterial infection means that the severity of a bacterial infection in a subject is reduced by about 1% to about 100% versus a subject to which a pharmaceutical composition or glycopeptide antibiotic of the present invention has not been administered. Preferably, the reduction in severity is a 100%, 99%, 98%, 97%, 96%, 95%, 90%, 80%, 70%, 60%, 50%, 40%, 30%, 20%, 10%, 5% or 1% reduction in severity. The severity of an infection may be based on the amount of bacteria present in a subject, the length of time that the bacteria can be detected in a subject, and/or the severity of a symptom of a bacterial infection, among other factors.

As used herein, the term "bi-weekly" refers to a frequency of every 13-15 days, the term "monthly" refers a frequency of every 28-31 days and "bi-monthly" refers a frequency of every 58-62 days.

As used herein, the term "contacting" is meant to broadly refer to bringing a bacterial cell and a molecule of a glycopeptide antibiotic of the present invention into sufficient proximity that the glycopeptide antibiotic can exert an effect on the bacterial cell. The glycopeptide antibiotic may be transported to the location of the bacterial cell, or the glycopeptide antibiotic may be situated in a location to which the bacterial cell travels or is brought into contact. The skilled artisan will understand that the term "contacting" includes physical interaction between a glycopeptide antibiotic and a bacterial cell, as well as interactions that do not require physical interaction.

In each aspect and embodiment of the present invention, the bacterial infection may be a Complicated Skin and Skin Structure Infection (cSSSI). Further, the bacteria and bacterial infections referred to herein in the methods of the present invention are those strains and species of bacterial against which the pharmaceutical compositions and glycopeptide antibiotics of the present invention, such as oritavancin, have activity. Specific examples of bacteria include those bacteria described in U.S. Pat. No. 5,840,684, gram positive bacteria, *Staphylococcus aureus* (methicillin-susceptible and -resistant strains; vancomycin-susceptible and -resistant strains), *Streptococcus pyogenes, Streptococcus agalactiae, Streptococcus anginosus* grp. (including *S. anginosus, S. intermedius*, and *S. constellatus*), *Streptococcus dysgalactiae* (including *S. dysgalactiae* subsp. *equisimilis*), *Streptococcus pneumoniae*, Streptococci species, including Streptococci Group A species, Streptococci Group B species, Streptococci Group C species, and Streptococci Group D species, Enterococci species, *Enterococcus faecalis* (vancomycin-susceptible and -resistant strains), *Enterococcus faecium* (vancomycin-susceptible and -resistant strains), *Staphylococcus epidermidis* (methicillin-susceptible and -resistant strains), *Staphylococcus haemolyticus*, all strains, species and subspecies of *Clostridium difficile*, including, for example, *C. difficile* PCR ribotypes 001, 106 and 027, and vegetative and spore forms of *Bacillus anthracis*.

The bacteria may be dormant bacteria, such as one or more of: (i) slow growing bacteria, (ii) stationary-phase bacteria and (iii) bacteria in biofilm form. Examples of bacteria that may be present or persist in a dormant state include *Staphylococcus aureus, Staphylococcus epidermidis*, a vancomycin-susceptible enterococci (such as vancomycin (VAN)-susceptible *Enterococcus faecalis* (VSE)), a vancomycin-resistant enterococci (such as VAN-resistant *E. faecalis* (VRE)), a *Staphylococcus* species (such as *Staph. epidermidis*) or a *Streptococcus* species.

EXAMPLES

Example 1

Evaluation of Oritavancin Activity In vitro in the Presence of Human and Mouse Serum Binding of drugs to serum components, typically serum albumin, is generally accepted to be an important determinant of pharmacokinetic and pharmacodynamic parameters. Estimates of serum protein binding are essential to translate drug exposure from non-clinical species to humans during assessments of toxicology, pharmacokinetics, and pharmacodynamics since the free fraction is thought to dictate drug activity (Bailey et al., *Antimicrob. Agents Chemother.* 35:1089-1092 (1991); Schmidt et al., *J. Pharm. Sci.* 99(3): 1107-1122 (2009); Schmidt et al., *Antimicrob Agents Chemother.* 52:3994-4000 (2008)). Recent evidence supports the concept of an "active fraction" that offers additional insight into the pharmacodynamic behavior of highly protein-bound drugs such as daptomycin (Tsuji et al., Determining the active fraction of daptomycin against MRSA by evaluating bactericidal activity in the presence of protein and pharmacodynamic (PD) modeling, abstr A1-1270/1. Abstr. 49th Intersci. Conf. Antimicrob. Agents Chemother. American Society for Microbiology, Washington, D.C. (2009)).

Because oritavancin exhibits a propensity to bind to surfaces of labware vessels, to filters and to dialysis membranes (Arhin et al. 2008. *Antimicrob. Agents Chemother.* 52:1597-1603), traditional biophysical methods used to measure serum protein binding are not suitable for assessing this agent. Microbiological methods that monitor the activity of an antibacterial agent in the presence of serum components against growing bacteria have also been used to estimate the proportion of free drug. Such methods include broth microdilution minimal inhibitory concentration (MIC) studies using arithmetic dilutions (Tsuji et al. 2008. *Diag. Microbiol. Infect. Dis.* 60:441-444). This method is advantageous for the study of oritavancin because the measurement of binding to serum components is performed under conditions that promote near-quantitative recovery of oritavancin (Arhin et al. 2008. *Antimicrob. Agents Chemother.* 52:1597-1603). Alternatively, the area under the inhibition curve (AUIC) has been used (Morrissey et al. 2006. 16th ECCMID, Nice, France. Apr. 1-4, 2006. Abstract P1584).

In the present study, binding of oritavancin, ceftriaxone and daptomycin to sera from three non-clinical species (mouse, rat and dog) and humans was assessed by two in vitro microbiological methods—the broth microdilution method using arithmetic dilutions of drugs and by time kill methodology.

Avid binding of oritavancin (ORI) to filtration and dialysis membranes renders most protein binding methodologies unsuitable. To control for any impact of serum components on bacterial growth and antibiotic activity, MIC shifts (from arithmetic drug dilutions) and area under the inhibitory curve (AUIC) shifts (from time-kill assays) were quantified in the presence of serum (SER) compared to SER ultrafiltrate (ULTRA; free of albumin) to estimate ORI binding to serum. In this manner, the extent of reduction in oritavancin activity in serum was related to its degree of serum protein binding. The method was benchmarked using daptomycin and ceftriaxone (Lee et al., *Antimicrob Agents Chemother.* 35:2505-2508 (1991); Schmidt et al., *Antimicrob Agents Chemother.* 52:3994-4000 (2008); Yuk et al., *Clin Pharmacokinet.* 17:223-235 (1989); McKay et al., Evaluation of oritavancin activity in vitro in the presence of human and mouse serum, abstr P1854. Abstr. 19th European Congress of Clinical Microbiology and Infectious Diseases. European Society of Clinical Microbiology and Infectious Diseases, Basel, Switzerland, May 16, 2009).

Pooled sera from humans, mice and rats were obtained from Equitech-Bio (Kerrville, Tex.); pooled serum from beagle dogs was from Bioreclamation (Liverpool, N.Y.). ULTRA was prepared using Centricon Plus-50 ultrafilters (Millipore, Billerica, Mass.), whose molecular weight cutoff (50 kDa) excludes albumin. ORI stock solutions were prepared following CLSI M100-818 (Clinical and Laboratory Standards Institute. 2008. CLSI document M100-S18). *Staphylococcus aureus* ATCC 29213 was used as the test isolate at a final inoculum of ~5×10$^5$ CFU/mL in both MIC and AUIC studies.

Method

Arithmetic MICs: Broth microdilution MIC assays with *Staphylococcus aureus* ATCC 29213 were based on CLSI guidelines (Clinical and Laboratory Standards Institute, 2009, CLSI document M7-A7). Growth media were 95% serum:5% CAMHB and 95% serum ultrafiltrate:5% CAMHB. Arithmetic dilutions of oritavancin and comparators were used to increase precision of minimum inhibitory concentration (MIC) values relative to doubling dilutions. Percent binding in serum was calculated as follows:

% Bound=(1−[mean MIC$_{ultrafiltrate}$/mean MIC$_{serum}$]×100%

AUIC studies: Time-kill studies were performed using *S. aureus* ATCC 29213 at a final inoculum of 1×10$^6$ CFU/mL in 95% serum:5% CAMHB and in 95% serum ultrafiltrate: 5% CAMHB. Oritavancin test concentrations were 2, 1 and 0.5 mg/L. Aliquots of time-kill cultures were removed at various time points and bacteria were enumerated by serial dilution plating. The AUIC was calculated using GraphPad Prism software. Percent binding in serum was calculated as follows:

% Bound=(1−[AUIC$_{ultrafiltrate}$/AUIC$_{serum}$]×100%

Results

The MICs for each condition, serum source, and test agent were precise (Table 1), with a mean coefficient of variation of 17%. MICs as determined under CLSI M7-A8 conditions ("CAMHB" columns, Table 1) (Clinical and Laboratory Standards Institute, 2009, CLSI document M7-A7) were within QC ranges (Clinical and Laboratory Standards Institute, 2009, CLSI document M100-819).

Increases in oritavancin MIC in serum compared to serum ultrafiltrate, by species, were similar across species (range, 5.5- to 7.8-fold; Table 2). Such shifts yielded similar mean values of oritavancin serum protein binding for the four species tested (range, 81.9% to 87.1%; Table 2). The 81.9% human serum protein binding estimate from the present study falls within the 79% to 89.9% range of previously reported values from growth-based (broth microdilution) or biophysical (dextran-coated charcoal adsorption; cantilever nanosensor) approaches (summarized in Table 3). These findings support the premise that growth-based methods can complement biophysical methods in estimation of the free fraction of antibiotics.

The 85.3% value of oritavancin binding to mouse serum protein concurs with the value of 85.2% that was derived by a similar approach using serum and serum ultrafiltrate (Table 3; W. A. Craig, unpublished data). Similarly, oritavancin was found to bind rat serum at 82.4% in the present study and rat plasma at greater than 80% by a broth microdilution approach (Table 3) (Zhanel et al., *Antimicrob. Agents Chemother.* 42:2427-2430 (1998)). Oritavancin binding was estimated at 87.1% to serum of beagle dog (Table 2), a species which had not been evaluated prior to the present study despite its importance in non-clinical toxicology assessments. These results showing a similar extent of oritavancin protein binding to human, mouse, rat and dog serum should facilitate translation of drug exposure between these species since the free fraction of oritavancin is likely to be equivalent across species, within the error of measurement of any single assay.

Assessment of area under the bacterial kill curves (MacGowan et al., *J. Chemother.* 16:23-29 (2004)) for oritavancin determined in the presence of serum compared to serum ultrafiltrate yielded protein binding values of 67.4, 63.9 and 61.7% for human serum (at 0.5, 1, and 2 μg/ml oritavancin, respectively) and of 66.5, 68.3 and 68.8% for mouse serum (at 0.5, 1, and 2 μg/ml oritavancin, respectively). While these estimates are lower than those derived from analysis of arithmetic MIC shifts in human and mouse serum noted above, they may be explained at least in part by the rapid killing kinetics of oritavancin (McKay et al., *J. Antimicrob. Chemother.* 63:1191-1199 (2009)) that cannot be surmised from the MIC shift endpoints of broth microdilution assays.

Ceftriaxone was highly bound to human serum (92.6%; Table 2), in agreement with both Yuk et al. (*Clin Pharmacokinet.* 17:223-235 (1989)) and MIC shift assessments by Schmidt et al. (*Antimicrob Agents Chemother.* 52:3994-4000 (2008)) but substantially higher than the 76.8% binding estimate derived from in vitro microdialysis (Schmidt et al., *Antimicrob Agents Chemother.* 52:3994-4000 (2008)). Variability in ceftriaxone serum protein binding across species (Rowe et al., In vitro protein binding of [14C]oritavancin in human plasma at 1, 10 and 91 μg/mL employing a dextran coated charcoal adsorption method, abstr. A2193. Abstr. 40th Intersci. Conf. Antimicrob. Agents Chemother., American Society for Microbiology, Washington, D.C., 2001; Schmidt et al., *Antimicrob Agents Chemother.* 52:3994-4000 (2008)) was also noted in the present study, with substantially lower binding estimates for serum from mouse, rat, and beagle dog (range, 20.9% to 37.5%) relative to human. These differences may result from true species-specific binding affinity differences (Rowe et al., In vitro protein binding of [14C]oritavancin in human plasma at 1, 10 and 91 μg/mL employing a dextran coated charcoal adsorption method, abstr. A2193. Abstr. 40th Intersci. Conf. Antimicrob. Agents Chemother., American Society for Microbiology, Washington, D.C., 2001) or from methodological differences during isolation or assay of serum from each species.

Daptomycin binding to serum protein also varied across species in the present study, ranging from 65.6% (rat) to 82.9% (human) (Table 2). For human serum, this value falls between the values of 58% reported by Tsuji et al. (Tsuji et al., *Diagn. Microbiol. Infect. Dis.* 60:441-444 (2008)) and 94% reported by Lee et al. (Lee et al., *Antimicrob Agents Chemother.* 35:2505-2508 (1991)). The implications of such variability are potentially important during translation of nonclinical findings to humans, for example, in pharmacokinetic-pharmacodynamic target attainment studies to support susceptibility breakpoint proposals (Mouton et al., Applying pharmacodynamics for susceptibility breakpoint selection and susceptibility testing. In, *Antimicrobial Pharmacodynamics in Theory and Clinical Practice*, pp. 21-44, Nightingale et al., Eds. Informa Healthcare, New York, N.Y., 2007).

While it is difficult to assess the accuracy of serum protein binding estimates from any single method, the precision of this cross-species comparative study, the concordance of single-species data from different methods, and the similarity of binding estimates across different species suggest that oritavancin is approximately 85% bound to serum protein and that differences in oritavancin protein binding across species are negligible. This conclusion is similar to one from studies of telavancin, another lipoglycopeptide, in which plasma protein binding was approximately 90% across tested species (Shaw et al., Protein binding of [14C]-telavancin in plasma and human skin blister fluid, abstr. A-1824. Abstr. 48th Intersci. Conf. Antimicrob. Agents Chemother./Infect. Dis. Soc. Am. 46th Annu. Meet. American Society for Microbiology, Washington, D.C. (2008)), although this value was substantially higher than the 62 to 70% estimates as determined using a growth-based assay (Tsuji et al., *Diagn. Microbiol. Infect. Dis.* 60:441-444 (2008)). The ca. 65% protein binding estimates from time kill-based assays with oritavancin (this study) support the idea that the 'active fraction' (Tsuji et al., Determining the active fraction of daptomycin against MRSA by evaluating bactericidal activity in the presence of protein and pharmacodynamic (PD) modeling, abstr A1-1270/1. Abstr. 49th Intersci. Conf. Antimicrob. Agents Chemother. American Society for Microbiology, Washington, D.C. (2009)) of oritavancin, namely its bioactive concentration in the presence of serum protein, is greater than the free fraction as predicted from biophysical approaches.

TABLE 1

Oritavancin, ceftriaxone and daptomycin MICs against *S. aureus* ATCC 29213 in cation-adjusted Mueller-Hinton broth, 95% serum ultrafiltrate and 95% serum from human, mouse, rat, and dog

| | | MIC (μg/ml) | | | | | | | | |
|---|---|---|---|---|---|---|---|---|---|---|
| | | Oritavancin[a] | | | Ceftriaxone[b] | | | Daptomycin[c] | | |
| Species | | CAMHB[d] | Ultrafiltrate[e] | Serum[f] | CAMHB | Ultrafiltrate | Serum | CAMHB | Ultrafiltrate | Serum |
| Human[g] | Mean | 0.084 | 0.140 | 0.775 | 4.88 | 2.88 | 38.8 | 0.975 | 0.513 | 3.00 |
| | SD | 0.005 | 0.038 | 0.324 | 0.835 | 0.354 | 11.0 | 0.046 | 0.125 | 0.535 |

TABLE 1-continued

Oritavancin, ceftriaxone and daptomycin MICs against *S. aureus* ATCC 29213 in cation-adjusted Mueller-Hinton broth, 95% serum ultrafiltrate and 95% serum from human, mouse, rat, and dog

| | | MIC (μg/ml) | | | | | | | | |
|---|---|---|---|---|---|---|---|---|---|---|
| | | Oritavancin[a] | | | Ceftriaxone[b] | | | Daptomycin[c] | | |
| Species | | CAMHB[d] | Ultrafiltrate[e] | Serum[f] | CAMHB | Ultrafiltrate | Serum | CAMHB | Ultrafiltrate | Serum |
| Mouse[h] | Mean | 0.105 | 0.079 | 0.538 | 5.00 | 3.75 | 6.00 | 0.975 | 3.00 | 12.5 |
| | SD | 0.030 | 0.004 | 0.052 | 0.816 | 0.500 | 1.16 | 0.05 | 0 | 2.89 |
| Rat[g] | Mean | 0.086 | 0.055 | 0.313 | 3.50 | 3.88 | 5.88 | 1.25 | 0.538 | 1.56 |
| | SD | 0.007 | 0.005 | 0.099 | 0.535 | 0.354 | 0.641 | 0.267 | 0.052 | 0.32 |
| Dog[g] | Mean | 0.080 | 0.061 | 0.475 | 5.25 | 1.09 | 1.38 | 1.00 | 0.638 | 2.50 |
| | SD | 0 | 0.014 | 0.046 | 0.707 | 0.582 | 0.518 | 0 | 0.150 | 0.530 |

[a]Arithmetic dilution steps of 0.5 μg/ml from 3 to 1 μg/ml, of 0.1 μg/ml from 1 to 0.3 μg/ml, of 0.05 μg/ml from 0.3 to 0.1 μg/ml and of 0.01 μg/ml from 0.1 to 0.04 μg/ml were prepared in cation-adjusted Mueller-Hinton broth containing 0.002% polysorbate-80.
[b]Arithmetic dilution steps of 10 μg/ml from 100 to 10 μg/ml and of 1 μg/ml from 10 to 1 μg/ml were prepared in cation-adjusted Mueller-Hinton broth.
[c]Arithmetic dilution steps of 5 μg/ml from 20 to 10 μg/ml, of 1 μg/ml from 10 to 2 μg/ml, of 0.5 μg/ml from 2 to 1 μg/ml and of 0.1 μg/ml from 1 to 0.3 μg/ml were prepared in cation-adjusted Mueller-Hinton broth supplemented with 50 μg/ml $CaCl_2$.
[d]As determined by CLSI M7-A8 guidelines in cation-adjusted Mueller-Hinton broth, supplemented with 0.002% polysorbate-80 (oritavancin) or 50 μg/ml $CaCl_2$ (daptomycin) (5).
[e]As determined in 95% serum ultrafiltrate + 5% cation-adjusted Mueller-Hinton broth.
[f]As determined in 95% serum + 5% cation-adjusted Mueller-Hinton broth.
[g]Means were derived from 8 replicates per condition per drug
[h]Means were derived from 4 to 8 replicates per condition per drug

TABLE 2

Serum-induced increases in broth microdilution MIC against *S. aureus* ATCC 29213, and corresponding protein binding estimates, for oritavancin, ceftriaxone and daptomycin

| | Oritavancin | | Ceftriaxone | | Daptomycin | |
|---|---|---|---|---|---|---|
| Species | Mean Fold MIC Increase[a] | % Bound[b] | Mean Fold MIC Increase[a] | % Bound[b] | Mean Fold MIC Increase[a] | % Bound[b] |
| Human | 5.5 | 81.9 | 13.5 | 92.6 | 5.8 | 82.9 |
| Mouse | 6.8 | 85.3 | 1.6 | 37.5 | 4.2 | 76.0 |
| Rat | 5.7 | 82.4 | 1.5 | 34.0 | 2.9 | 65.6 |
| Dog | 7.8 | 87.1 | 1.3 | 20.9 | 3.9 | 74.5 |

[a]Ratio of the mean arithmetic MIC in 95% serum to the mean arithmetic MIC in 95% serum ultrafiltrate
[b]Calculated from mean MICs using the formula: Percent Protein Bound = (1 − [MIC in ultrafiltrate/MIC in serum]) × 100%

TABLE 3

Oritavancin serum protein binding estimates for human, mouse, rat, and dog

| Species | Matrix | Protein Binding[a] (%) | Method | Oritavancin Concentration | Reference |
|---|---|---|---|---|---|
| Human | Plasma | 87.5 | Broth microdilution | Various | Zhanel et al. 1998[d] |
| | Plasma | 85.7–89.9 | DCC[b] adsorption | 1–91 μg/ml | Rowe and Brown 2001[e] |
| | Serum | 79.6 | Broth microdilution | Various | Craig, unpublished |
| | Albumin | 79 ± 0.2 | Cantilever nanosensor[c] | 0.2 μg/ml | McKendry, unpublished |
| | Serum | 81.9 | Broth microdilution | Various | This study |
| Mouse | Serum | 85.2 | Broth microdilution | Various | Craig, unpublished |
| | Serum | 85.3 | Broth microdilution | Various | This study |
| Rat | Plasma | >80 | Broth microdilution | Various | Zhanel et al. 1998[d] |
| | Serum | 82.4 | Broth microdilution | Various | This study |
| Dog | Serum | 87.1 | Broth microdilution | Various | This study |

[a]Standard deviation values are provided where available
[b]Dextran-coated charcoal
[c]Ndieyira et al., *Nature Nanotechnol.* 3: 691–696 (2008)
[d]Zhanel et al., *Antimicrob. Agents Chemother.* 42: 2427–2430 (1998)
[e]Rowe and Brown, In vitro protein binding of [14C]oritavancin in human plasma at 1, 10 and 91 μg/mL employing a dextran coated charcoal adsorption method, abstr. A2193. Abstr. 40th Intersci. Conf. Antimicrob. Agents Chemother., American Society for Microbiology, Washington, DC 2001

Example 2

Measurement of Glycopeptide Antibiotics Bounds to Serum Proteins by Equilibrium Dialysis A known concentration (normally bracketing a physiologically-relevant range; e.g. 0.01 to 100 μg/mL) and volume (100-500 μL) of antibiotic in human serum is placed into the sample chamber of a Rapid Equilibrium Dialysis apparatus (Thermo Scientific). The MWCO of the dialysis membrane in the device, 8,000, excludes albumin and large serum proteins. A known volume (300-750 μL) of buffer such as phosphate-buffered saline is then placed in the buffer compartment. The unit is covered with sealing tape and incubated at 37° C. at approximately 100 rpm on an orbital shaker or 20 rpm on an up-and-down shaker for 4 hours so as to achieve equilibrium. The seal is removed and equal volumes (e.g. 100 μL, 100 μL) are removed from both the buffer and the plasma chambers, transferred to eppendorf tubes and subjected to liquid chromatography/mass spectrometry (LC/MS) analysis for the antibiotic as follows: samples are centrifuged for 10 minutes at 13,000-15,000×g and 50 μL of each is transferred into separate microcentrifuge tubes. A total of 50 μL of plasma is added to the buffer sample, and 50 μL of PBS is added to the collected plasma sample. 300 μL of precipitation buffer (such as cold 90/10 acetonitrile/water with 0.1% formic acid) is added to precipitate protein and release compound. Samples are vortexed vigorously and incubated 30 minutes on ice. Supernatants are transferred to a vial or plate for analysis; appropriate internal standards are added and the antibiotic is quantitated by LC/MS. Alternatively, the supernatant can be dried and the antibiotic reconstituted before LC/MS. The concentration of test compound in the buffer and plasma chambers from peak areas relative to the internal standard are calculated. To calculate the percentage of the test compound bound to serum protein, the following formulae are used: % Free=(Concentration buffer chamber/Concentration plasma chamber)×100% and % Bound=100%−% Free.

Example 3

Measurement of Glycopeptide Antibiotics Bounds to Serum Proteins by Ultrafiltration As in the equilibrium dialysis assay described above in Example 2, a known concentration and volume of analyte is spiked into a known volume of serum (or a known concentration and volume of purified serum albumin) and the sample is transferred into the ultrafiltration apparatus. A convenient assay platform is the 96-well Millipore MultiScreen Ultracel-PPB (plasma protein binding) plate with a dialysis membrane having an MWCO of 10,000 and requiring sample volumes in the 100-300 μL range. After ultrafiltration, the analyte in the ultrafiltrate is quantitated by LC/MS as above in Example 2.

Example 4

Measurement of Glycopeptide Antibiotics Bounds to Serum Proteins by Ultracentrifugation A mixture of analyte plus albumin (or analyte in serum) is subjected to ultracentrifugation in a manner that sediments protein-bound analyte and leaves free analyte in solution. After the centrifugation step has been completed, supernatant is carefully removed from the ultracentrifugation tubes and analyte is quantitated by LC/MS as above in Example 2.

The invention of this application has been described above both generically and with regard to specific embodiments. Although the invention has been set forth in what is believed to be the preferred embodiments, a wide variety of alternatives known to those of skill in the art can be selected within the generic disclosure. The invention is not otherwise limited, except for in the recitation of the claims.

All documents, publications, patents, books, manuals, articles, papers, abstracts, posters and other materials referenced herein are expressly incorporated herein by reference in their entireties.

We claim:

1. A method of treating a bacterial infection in a human subject, comprising administering a therapeutically effective amount of a glycopeptide antibiotic to the human subject having the bacterial infection,
    wherein the glycopeptide antibiotic is oritavancin, or a pharmaceutically acceptable salt, hydrate, or solvate thereof, or a mixture thereof,
    wherein the effective amount of the glycopeptide antibiotic is between about 15 and 50 mg/kg body weight,
    wherein the effective amount of the glycopeptide antibiotic provides a fraction of glycopeptide antibiotic bound to serum proteins in the subject in the range of about 50% to about 95%, and
    wherein the fraction of glycopeptide antibiotic bound to serum proteins is determined from serum obtained from the subject.

2. The method of claim 1, wherein the fraction of the glycopeptide antibiotic bound to serum proteins is in the range of about 55% to about 65%.

3. The method of claim 1, wherein the fraction of the glycopeptide antibiotic bound to serum proteins is in the range of about 80% to about 90%.

4. The method of claim 1, wherein the fraction of the glycopeptide antibiotic bound to serum proteins is in the range of about 70% to about 90%.

5. The method of claim 1, wherein the fraction of glycopeptide antibiotic bound to serum proteins is determined from serum obtained from the subject about 30 minutes after completion of the administration of the glycopeptide antibiotic.

6. The method of claim 1, wherein the fraction of glycopeptide antibiotic bound to serum proteins is determined from serum obtained from the subject about 24 hours after completion of the administration of the glycopeptide antibiotic.

7. The method of claim 1, wherein the bacterial infection is a Complicated Skin and Skin Structure Infection (cSSSI).

8. The method of claim 1, wherein the glycopeptide antibiotic is in the form of a pharmaceutical composition comprising the glycopeptide antibiotic and a pharmaceutically acceptable carrier or diluent.

9. The method of claim 1, wherein said administering is via intravenous administration or oral administration.

10. A method of treating a bacterial infection in a subject, comprising administering a therapeutically effective amount of a glycopeptide antibiotic to the subject having, the bacterial infection, wherein the glycopeptide antibiotic is oritavancin, or a pharmaceutically acceptable salt, hydrate, or solvate thereof, or a mixture thereof, wherein the effective amount of the glycopeptide antibiotic is between about 15 and 50 mg/kg body weight, wherein the effective amount of the glycopeptide antibiotic provides a mean fraction of glycopeptide antibiotic bound to serum proteins in the subject in a range of about 50% to about 95% from a mean of about 30 minutes to about 24 hours after completion of administration of the glycopeptide antibiotic, and wherein the fraction of glycopeptide antibiotic bound to serum proteins is determined from serum obtained from the subject.

11. The method of claim 10, wherein the fraction of the glycopeptide antibiotic bound to serum proteins is in a range of about 55% to about 65%.

12. The method of claim 10, wherein the fraction of the glycopeptide antibiotic bound to serum proteins is in a range of about 80% to about 90%.

13. The method of claim 10, wherein the fraction of the glycopeptide antibiotic bound to serum proteins is in a range of about 70% to about 90%.

14. The method of claim 10, wherein the mean fraction of glycopeptide antibiotic bound to serum proteins is determined from serum obtained from the subject by calculating a mean value of nine measurements comprising:
  (i) a first measurement of a fraction of glycopeptide antibiotic bound to serum proteins determined from serum obtained from the subject at about 30 minutes after completion of administration of the glycopeptide antibiotic,
  (ii) a second measurement of a fraction of glycopeptide antibiotic bound to serum proteins determined from serum obtained from the subject at about 1.5 hours after completion of administration of the glycopeptide antibiotic,
  (iii) a third measurement of a fraction of glycopeptide antibiotic bound to serum proteins determined from serum obtained from the subject at about 2.5 hours after completion of administration of the glycopeptide antibiotic,
  (iv) a fourth measurement of a fraction of glycopeptide antibiotic bound to serum proteins determined from serum obtained from the subject at about 3.5 hours after completion of administration of the glycopeptide antibiotic,
  (v) a fifth measurement of a fraction of glycopeptide antibiotic bound to serum proteins determined from serum obtained from the subject at about 4.5 hours after completion of administration of the glycopeptide antibiotic,
  (vi) a sixth measurement of a fraction of glycopeptide antibiotic bound to serum proteins determined from serum obtained from the subject at about 5.5 hours after completion of administration of the glycopeptide antibiotic,
  (vii) a seventh measurement of a fraction of glycopeptide antibiotic bound to serum proteins determined from serum obtained from the subject at about 6.5 hours after completion of administration of the glycopeptide antibiotic,
  (viii) an eighth measurement of a fraction of glycopeptide antibiotic bound to serum proteins determined from serum obtained from the subject at about 12 hours after completion of administration of the glycopeptide antibiotic, and
  (ix) a ninth measurement of a fraction of glycopeptide antibiotic bound to serum proteins determined from serum obtained from the subject at about 24 hours after completion of administration of the glycopeptide antibiotic.

15. The method of claim 10, wherein the bacterial infection is a Complicated Skin and Skin Structure Infection (cSSSI).

16. The method of claim 10, wherein the glycopeptide antibiotic is in the form of a pharmaceutical composition comprising the glycopeptide antibiotic and a pharmaceutically acceptable carrier or diluent.

17. The method of claim 10, wherein said administering is via intravenous administration or oral administration.

* * * * *